US008951763B2

(12) United States Patent
Kim et al.

(10) Patent No.: US 8,951,763 B2
(45) Date of Patent: *Feb. 10, 2015

(54) METHOD FOR PREPARING 3-HYDROXYPROPIONIC ACID FROM GLYCEROL IN HIGH YIELD

(75) Inventors: Chul Ho Kim, Daejeon (KR); Jeong-Woo Seo, Daejeon (KR); Lianhua Luo, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/698,936

(22) PCT Filed: May 24, 2011

(86) PCT No.: PCT/KR2011/003798
§ 371 (c)(1), (2), (4) Date: Dec. 28, 2012

(87) PCT Pub. No.: WO2011/149248
PCT Pub. Date: Dec. 1, 2011

(65) Prior Publication Data
US 2013/0095541 A1    Apr. 18, 2013

(30) Foreign Application Priority Data
May 25, 2010    (KR) .................. 10-2010-0048492

(51) Int. Cl.
*C12P 7/42*    (2006.01)
*C12N 15/74*    (2006.01)
(Continued)

(52) U.S. Cl.
CPC ............... *C12N 15/746* (2013.01); *C12N 1/32* (2013.01); *C12N 15/52* (2013.01); *C12P 7/42* (2013.01)
USPC .................. 435/146; 435/252.3; 435/471

(58) Field of Classification Search
None
See application file for complete search history.

(56) References Cited

U.S. PATENT DOCUMENTS 5,321,156 A    6/1994    Behr et al.
5,831,121 A    11/1998    Haas et al.
(Continued)

FOREIGN PATENT DOCUMENTS

EP    1731604 A1    12/2006
JP    2000-159724 A    6/2000
(Continued)

OTHER PUBLICATIONS

Luo et al., "Identification and characterization of the propanediol utilization protein PduP of *Lactobacillus reuteri* for 3-hydroxypropionic acid production from glycerol", Appl. Microbiol. Biotechnol., 89:697-703, 2011.*

(Continued)

*Primary Examiner* — Rebecca Prouty
*Assistant Examiner* — Richard Ekstrom
(74) *Attorney, Agent, or Firm* — Hultquist, PLLC; Mary B. Grant

(57) ABSTRACT

The present invention relates to a method for producing 3-hydroxypropionic acid by culturing in a glycerol-containing medium a mutant microorganism obtained by inserting or amplifying a gene encoding propanediol utilization protein in a microorganism having the abilities to produce coenzyme B12 and produce 3-hydroxypropionic acid using glycerol as a carbon source.

According to the present invention, 3-hydroxypropionic acid can be produced in high yield from glycerol without having to add expensive coenzyme B12 as a cofactor.

3 Claims, 3 Drawing Sheets

(51) Int. Cl.
*C12N 1/32* (2006.01)
*C12N 15/52* (2006.01)

(56) References Cited

U.S. PATENT DOCUMENTS

| | | | |
|---|---|---|---|
| 6,013,494 A * | 1/2000 | Nakamura et al. | 435/158 |
| 6,432,686 B1 * | 8/2002 | Bulthuis et al. | 435/158 |
| 6,803,218 B1 * | 10/2004 | Seyfried et al. | 435/158 |
| 6,852,517 B1 | 2/2005 | Suthers et al. | |
| 6,953,684 B2 * | 10/2005 | Dunn-Coleman et al. | 435/252.3 |
| 7,074,608 B1 | 7/2006 | Dunn-Coleman et al. | |
| 7,267,972 B2 * | 9/2007 | Sarcabal et al. | 435/232 |
| 7,504,250 B2 * | 3/2009 | Emptage et al. | 435/252.3 |
| 7,524,660 B2 * | 4/2009 | Caimi et al. | 435/159 |
| 7,582,457 B2 * | 9/2009 | Dunn-Coleman et al. | 435/158 |
| 7,629,161 B2 * | 12/2009 | Laffend et al. | 435/252.3 |
| 7,745,184 B2 * | 6/2010 | Cervin et al. | 435/158 |
| 7,858,355 B2 * | 12/2010 | Sarcabal et al. | 435/232 |
| 8,338,148 B2 * | 12/2012 | Kim et al. | 435/158 |
| 2007/0148749 A1 * | 6/2007 | Yasuda et al. | 435/158 |
| 2008/0131945 A1 * | 6/2008 | Toraya et al. | 435/141 |
| 2010/0021978 A1 * | 1/2010 | Burk et al. | 435/146 |
| 2011/0021768 A1 * | 1/2011 | Gibson et al. | 536/23.2 |
| 2011/0256598 A1 * | 10/2011 | Eliot et al. | 435/146 |
| 2012/0270287 A1 * | 10/2012 | Kim et al. | 435/146 |
| 2012/0301935 A1 * | 11/2012 | Yu et al. | 435/146 |

FOREIGN PATENT DOCUMENTS

| | | | |
|---|---|---|---|
| JP | 2010183858 A * | 8/2010 | |
| KR | 10-2002-0000030 A | 1/2002 | |
| WO | WO 2010064744 A1 * | 6/2010 | |
| WO | WO 2010104224 A1 * | 9/2010 | |
| WO | WO 2011052819 A1 * | 5/2011 | |

OTHER PUBLICATIONS

Leal et al., "PduP is a coenzyme-a-acylating propionaldehyde dehydrogenase associated with the polyhedral bodies involved in B12-dependent 1,2-propanediol degradation by *Salmonella enterica serovar Typhimurium* LT2", Arch. Microbiol., 180: 353-361, 2003.*

Kwak et al., "Biosynthesis of 3-hydroxypropionic acid from glycerol in recombinant *Escherichia coli* expressing *Lactobacillus brevis* dhaB and dhaR gene clusters and *E. coli* K-1 aldH", Bioresource Technology, 135: 432-439, 2013.*

Andreessen et al., "Conversion of glycerol to poly(3-hydroxypropionate) in recombinant *Escherichia coli*", Applied Environmental Microbiology, vol. 76, No. 2, 622-626, 2010.*

Luo et al., "Stimulation of reductive glycerol metabolism by overexpression of an aldehyde dehydrogenase in a recombinant *Klebsiella pneumoniae* strain defective in the oxidative pathway", J. Ind. Microbiol. Biotechnol., 38: 991-999, 2011.*

Raj, S., et al., "Production of 3-Hydroxypropionic Acid From Glycerol by a Novel Recombinant *Escherichia Coli* BL21 Strain", "Process Biochemistry", Dec. 1, 2008, pp. 1440-1446, vol. 43, No. 12.

Rathnasingh, C., et al., "Development and Evaluation of Efficient Recombinant *Escherichia Coli* Strains for the Production of 3-Hydroxypropionic Acid From Glycerol", "Biotechnology Bioengineering", Jun. 4, 2009, pp. 729-739, vol. 104, No. 4.

* cited by examiner

US 8,951,763 B2

METHOD FOR PREPARING 3-HYDROXYPROPIONIC ACID FROM GLYCEROL IN HIGH YIELD

CROSS-REFERENCE TO RELATED APPLICATIONS

This application is a U.S. national phase application under the provisions of 35 U.S.C. §371 of International Patent Application No. PCT/KR2011/003798 filed May 24, 2011, which in turn claims priority of Korean Patent Application No. 10-2010-0048492 filed May 25, 2010. The disclosures of such international patent application and Korean priority patent application are hereby incorporated herein by reference in their respective entireties, for all purposes.

TECHNICAL FIELD

The present invention relates to a method for producing 3-hydroxypropionic acid by culturing in a glycerol-containing medium a mutant microorganism obtained by inserting or amplifying a gene encoding propanediol utilization protein in a microorganism having the abilities to produce coenzyme B12 and produce 3-hydroxypropionic acid using glycerol as a carbon source

BACKGROUND ART 3-hydroxypropionic acid which receives attention as a biomass-derived platform chemical together with lactic acid and succinic acid and can be used as a raw material for the preparation of 1,3-propanediol, acrylic acid, acrylamide, malonic acid or a biopolymer such as poly-hydroxypropionic acid. Therefore, the development of technology for producing large amounts of 3-hydroxypropionic acid is very important.

Known chemical processes for the production of 3-hydroxypropionic acid include a process of producing 3-hydroxypropionic acid from 1,3-propanediol in the presence of a palladium catalyst (U.S. Pat. No. 5,321,156), a process of producing 3-hydroxypropionic acid from 3-hydroxypropionaldehyde in the presence of a palladium/platinum catalyst (U.S. Pat. No. 5,831,121), a process of producing 3-hydroxypropionic acid using an ion exchange resin (Japanese Patent Publication No. 2000-159724), and a process of producing 3-hydroxypropionic acid from epoxide derivatives in the presence of an acid or base catalyst (Korean Patent No. 10-0408806).

With respect to biological methods, Suthers et al. of the University of Wisconsin reported a method of producing 3-hydroxypropionic acid from glycerol using a recombinant *E. coli* strain that overexpresses a glycerol dehydratase gene derived from *Klebsiella pneumoniae* and an aldehyde dehydrogenase gene derived from *E. coli* or *Saccharomyces cerevisiae* (U.S. Pat. No. 6,852,517). Recently, Rathnasingh et al. reported a novel recombinant *E. coli* strain that produces increased amounts of 3-hydroxypropionic acid from glycerol (Rathnasingh et al., Biotechnol. Bineng. 104:729-39. 2009).

However, the method of producing 3-hydroxypropionic acid from glycerol using the recombinant *E. coli* strain has a disadvantage in that the expensive coenzyme adenosylcobalamine (coenzyme B12) is required to be supplied to a culture medium in order to reactivate the glycerol dehydratase enzyme.

Meanwhile, the present inventors found that, when the aldehyde dehydrogenase gene in *Klebsiella pneumoniae* is highly expressed, 3-hydroxypropionic acid can be produced with high productivity without having to add coenzyme 12.

Accordingly, the present inventors have made extensive efforts to a method of producing an increased amount of 3-hydroxypropionic acid from glycerol by *Klebsiella pneumoniae* and, and as a result, have found that, when the gene encoding propanediol utilization protein of *Lactobacillus reuteri* is overexpressed in *Klebsiella pneumoniae*, 3-hydroxypropionic acid can be produced in high yield by the mutant *Klebsiella pneumoniae* strain, thereby completing the present invention.

DISCLOSURE OF INVENTION

It is an object of the present invention to provide a method of producing 3-hydroxypropionic acid in high yield from glycerol.

Another object of the present invention is to provide a mutant microorganism capable of producing 3-hydroxypropionic acid in high yield from glycerol.

To achieve the above object, the present invention provides a mutant microorganism obtained by introducing or amplifying a gene encoding propanediol utilization protein in a microorganism having the abilities to produce coenzyme B12 and produce 3-hydroxypropionic acid using glycerol as a carbon source.

The present invention also provides a method for preparing a mutant microorganism having a high ability to produce 3-hydroxypropionic acid, the method comprising introducing or amplifying a gene encoding propanediol utilization protein in a microorganism having the abilities to produce coenzyme B12 and produce 3-hydroxypropionic acid using glycerol as a carbon source.

The present invention also provides a method for producing 3-hydroxypropionic acid, the method comprising the steps of: (a) culturing the above mutant microorganism in a glycerol-containing medium, thereby producing 3-hydroxypropionic acid; and (b) recovering the produced 3-hydroxypropionic acid.

The present invention also provides a *Klebsiella pneumoniae* mutant obtained by deleting a glycerol dehydrogenase gene (DhaD), a transcriptional activator gene (DhaR), a 1,3-propanediol oxidoreductase gene (DhaT) and a glycerol dehydratase reactivation factor II gene (DhaBA2) from *Klebsiella pneumoniae* and introducing a 1,3-propanediol oxidoreductase-encoding gene, an aldehyde dehydrogenase-encoding gene and a propanediol utilization protein gene into the *Klebsiella pneumoniae*.

The present invention also provides a method for preparing a *Klebsiella pneumoniae* mutant, the method comprising deleting a glycerol dehydrogenase gene (DhaD), a transcriptional activator gene (DhaR), a 1,3-propanediol oxidoreductase gene (DhaT) and a glycerol dehydratase reactivation factor II gene (DhaBA2) from *Klebsiella pneumoniae* and introducing a 1,3-propanediol oxidoreductase-encoding gene, an aldehyde dehydrogenase-encoding gene and a propanediol utilization protein gene into the *Klebsiella pneumoniae*.

The present invention also provides a method for producing 3-hydroxypropionic acid, the method comprising the steps of: (a) culturing the above *Klebsiella pneumoniae* mutant in a glycerol-containing medium, thereby producing 3-hydroxypropionic acid; and (b) recovering the produced 3-hydroxypropionic acid.

Other features and embodiments of the present invention will be more apparent from the following detailed descriptions and the appended claims

BEST MODE FOR CARRYING OUT THE INVENTION

Figure 1:
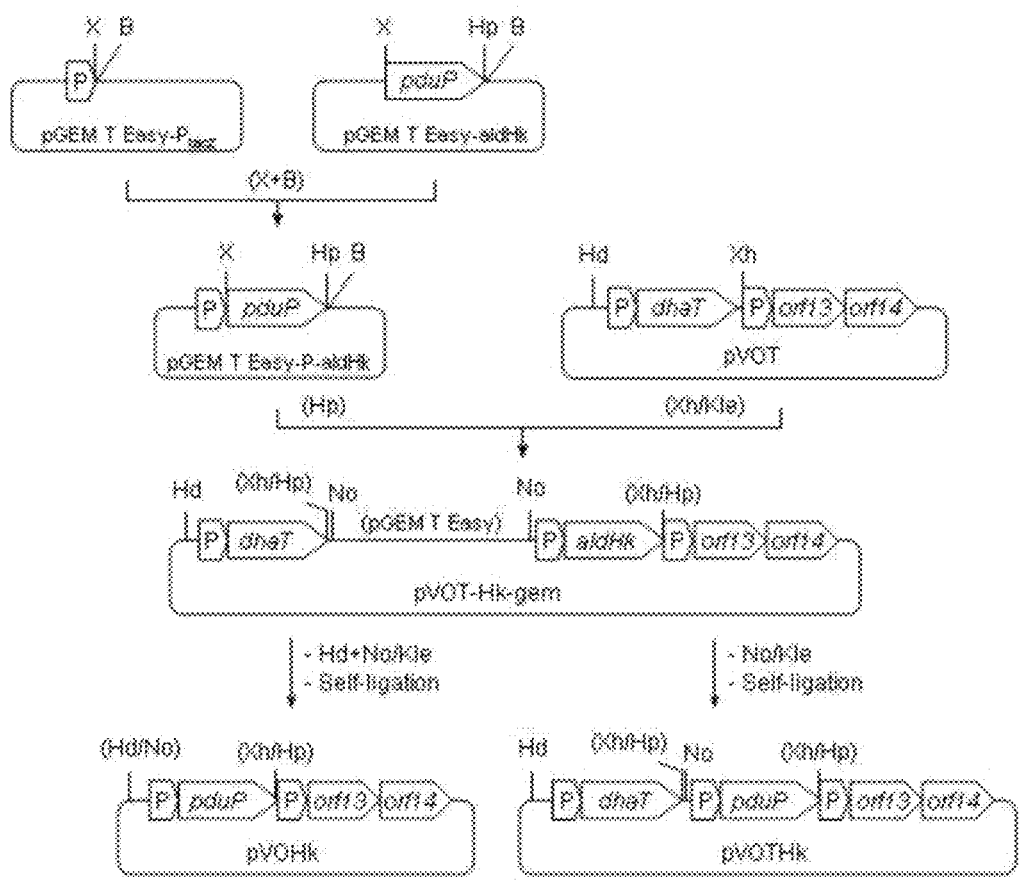
FIG. 1 is a diagram representing a process for constructing the recombinant plasmid pVOTLp.

Unless defined otherwise, all technical and scientific terms used herein have the same meaning as commonly understood by one of ordinary skill in the art to which the invention pertains. Generally, the nomenclature used herein and the experiment methods which will be described later are those well known and are commonly employed in the art.

In one aspect, the present invention is directed to a mutant microorganism obtained by introducing or amplifying a gene encoding propanediol utilization protein in a microorganism having the abilities to produce coenzyme B12 and produce 3-hydroxypropionic acid using glycerol as a carbon source, and a method for preparing the same.

In the present invention, the gene encoding propanediol utilization protein may be the gene encoding propanediol utilization protein (PduP) of *Lactobacillus reuteri*, and the microorganism having the abilities to produce coenzyme B12 and produce 3-hydroxypropionic acid using glycerol as a carbon source may be a microorganism of the genus *Klebsiella*. In the present invention, the microorganism having the abilities to produce coenzyme B12 and produce 3-hydroxypropionic acid using glycerol as a carbon source may be a microorganism in which the glycerol oxidative pathway was blocked.

In another aspect, the present invention is directed to a method for producing 3-hydroxypropionic acid, the method comprising the steps of: (a) culturing the above mutant microorganism in a glycerol-containing medium, thereby producing 3-hydroxypropionic acid; and (b) recovering the produced 3-hydroxypropionic acid.

In still another aspect, the present invention is directed a *Klebsiella pneumoniae* mutant obtained by deleting a glycerol dehydrogenase gene (DhaD), a transcriptional activator gene (DhaR), a 1,3-propanediol oxidoreductase gene (DhaT) and a glycerol dehydratase reactivation factor II gene (DhaBA2) from *Klebsiella pneumoniae* and introducing a 1,3-propanediol oxidoreductase-encoding gene, an aldehyde dehydrogenase-encoding gene and a propanediol utilization protein gene into the *Klebsiella pneumoniae*, and a method for preparing the same.

In the present invention, the gene encoding propanediol utilization protein may be the gene encoding propanediol utilization protein (PduP) of *Lactobacillus reuteri*, and the *Klebsiella pneumoniae* mutant may be *Klebsiella pneumoniae* AK-VOTLp (KCTC 11689BP).

In a further aspect, the present invention is directed a method for producing 3-hydroxypropionic acid, the method comprising the steps of: (a) culturing the above *Klebsiella pneumoniae* mutant in a glycerol-containing medium, thereby producing 3-hydroxypropionic acid; and (b) recovering the produced 3-hydroxypropionic acid.

In the present invention, recovery of 3-hydroxypropionic acid from the culture broth of the mutant can be carried out using conventional isolation techniques including, for example, distillation, electrodialysis, evaporation, chromatography, solvent extraction, and reaction extraction, and these techniques may generally be used in combination to isolate highly pure substances.

As used herein, the expression "amplification" of a gene means additionally introducing a gene present in either the chromosome of an individual or a plasmid so as to be capable of being overexpressed, and the expression "introduction" of a gene means inserting a gene into the chromosome of an individual or transforming a gene into an individual using a recombinant vector.

In the present invention, insertion of the gene into the chromosome of a cell can be carried out using a conventional gene manipulation method known in the art. For example, insertion of the gene can be carried out using a retroviral vector, an adenoviral vector, an adeno-associated viral vector, a herpes simplex viral vector, a poxvirus vector, a lentiviral vector or a non-viral vector.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Construction of *Klebsiella pneumoniae* Recombinant Strain in which Gene Encoding Propanediol Utilization Protein was Overexpressed (1) Construction of Plasmids that Overexpress Gene Encoding Propanediol Utilization Protein A gene encoding propanediol utilization protein was believed to be involved in the production of 3-hydroxypropionic acid from glycerol in a *Klebsiella pneumoniae* strain. Thus, plasmids for overexpressing the gene encoding propanediol utilization protein in *Klebsiella pneumoniae* were constructed.

Specifically, the gene encoding propanediol utilization protein (PduP) (GenBank database No. BAG26139) was amplified using the chromosomal DNA of *Lactobacillus reuteri* as a template and the following primer sequences, and the amplification product was cloned into a pGEM TEasy vector and sequenced. Using the resulting vector, plasmid DNAs were constructed (see FIG. 1).

SEQ ID NO: 1:
5'-TCTAGAatgcagattaatgatattgaaagtgct-3'
(PduP-F)

SEQ ID NO: 2:
5'-GGATCCCTCGAGttaataccagttacgtactgagaatcc-3'
(AldHk-R)

As shown in FIG. 1, the gene encoding propanediol utilization protein (PduP) of *Lactobacillus reuteri* was introduced downstream of the lacZ promoter, and then inserted into the plasmid pVOT containing the DhaB reactivation enzyme gene (dhaT) and the 1,3-propanediol oxidoreductase gene (DhaT), thereby constructing the plasmid pVOTLp containing the gene encoding propanediol utilization protein and the DhaB reactivation enzyme gene.

Each of the constructed pVOTLp and the plasmid pVOT was introduced into a plasmid DNA-cured *Klebsiella pneumoniae* MGH78578 strain (named "Cu") thereby constructing *Klebsiella pneumoniae* Cu/pVOT and *Klebsiella pneumoniae* Cu/pVOTLp.

Figure 2:
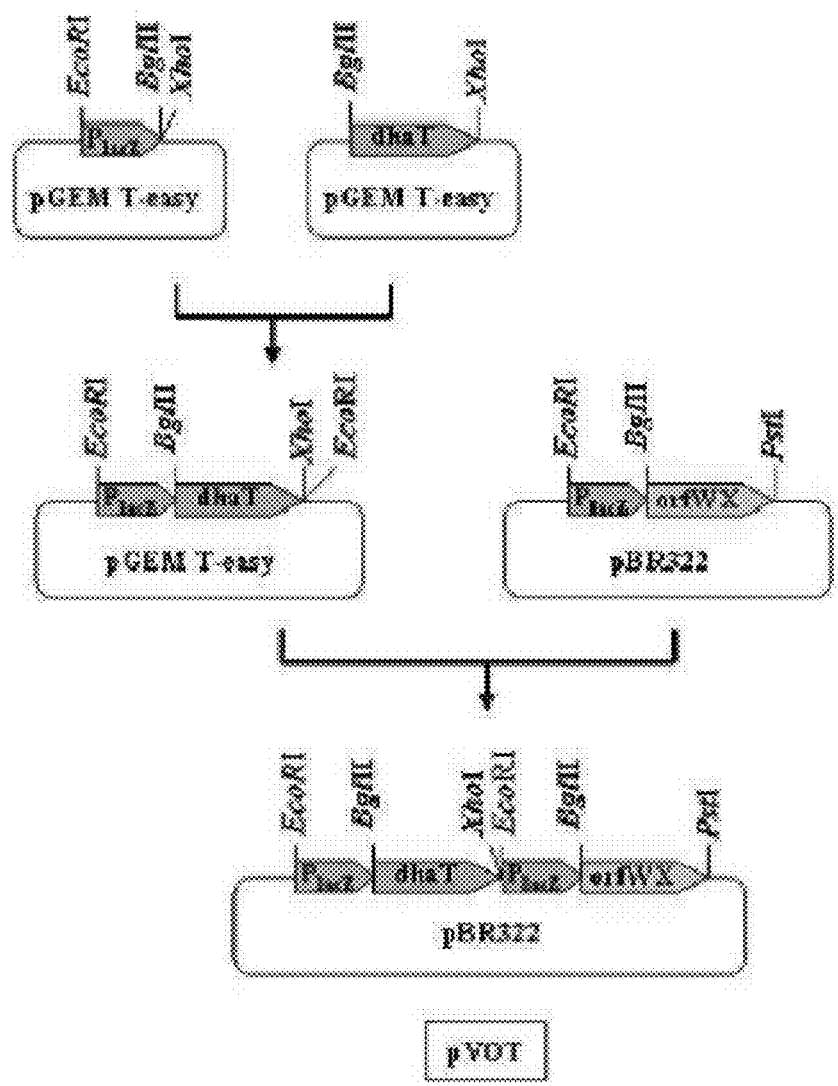
FIG. 2 is a diagram representing a process for constructing the recombinant plasmid pVOT.

The pVOT plasmid was constructed according to the method shown in FIG. 2. The plasmid pVOT was introduced into *Klebsiella pneumoniae* and named "*Klebsiella pneumoniae* AK-VOT". This recombinant strain was deposited at the Biological Resource Center in the Korea Research Institute of Bioscience and Biotechnology under accession number KCTC 11421BP.

(2) Construction of *Klebsiella pneumoniae* Recombinant Strain in which Glycerol Oxidative-Reductive Pathways were Broken The DhaB enzyme reactivation gene, DhaT gene, DhaR regulator and DhaD gene of the dha regulon (see FIG. 2) were substituted with the apramycin-resistant gene by a homologous recombination method using a plasmid DNA-cured *Klebsiella pneumoniae* MGH78578 strain (named "Cu") as a parent strain, thereby preparing the recombinant strain AK having deletions of both the glycerol oxidative and reductive pathways.

DNA fragments for preparing a plasmid for homologous recombination were amplified by PCR using the chromosomal DNA of the *Klebsiella pneumoniae* MGH78578 strain as a template and the following primer sets:

Primers for amplification of dhaBI gene fragments

```
SEQ ID NO: 3:
5'-TCTAGAATGAAAAGATCAAAACGATTT-3'
(dhaBI XbaI-480bpF)

SEQ ID NO: 4:
5'-GGATCCGTCAGCGGCAATCTGCAC-3'
(dhaBI BamHI-480bpR)
```

Primers for Amplification of dhaK Gene Fragments

```
SEQ ID NO: 5:
5'-AAGCTTCATGCTCTCCGGCGCCTGTC-3'
(dhaK HindIII-200-700 bpF)

SEQ ID NO: 6:
5'-AGATCTATTTGGTCCAGCGAGCTGAAGC-3'
(dhaK BglII-200-700bpR)
```

Primers for Amplification of dhaR Gene Fragments

```
SEQ ID NO: 7:
5'-AGATCTCCTGGGATTTCGCGACGGCA-3'
(dhaR bglII-200-700bpF)

SEQ ID NO: 8:
5'-AAGCTTTCGACAATCGGTTTTAAGGTG-3'
(dhaR HindIII-200-700bpR)
```

Primers for Amplification of Apr Gene Fragments

```
SEQ ID NO: 9:
5'-GTTAACCTGACGCCGTTGGATACACC-3'
Apr HpaI F

SEQ ID NO: 10:
5'-AGATCTAAAAGCTTATGAGCTCAGCCAATCGA-3'
Apr HindIII-BglIIR
```

The amplified DNA fragments were cloned into a pGEM TEasy vector and sequenced. Then, as shown in FIG. 3, a plasmid DNA was constructed using the vector.

Figure 3:
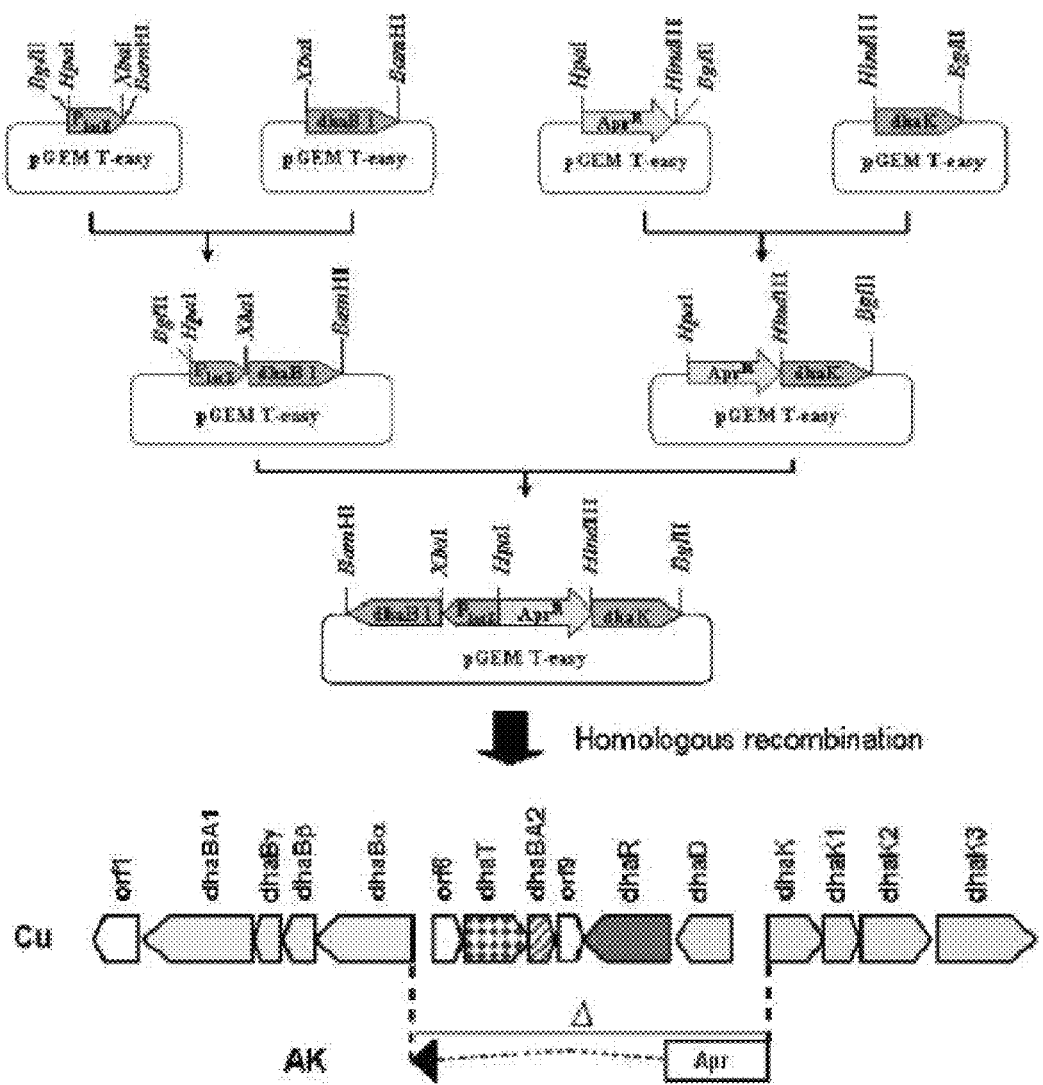
FIG. 3 is a diagram representing a process for constructing a *Klebsiella pneumoniae* AK mutant strain.

In the method shown in FIG. 3, the plasmid DNA for preparing the AK strain comprising a linkage of DhaB gene amino terminus (dhaB')-LacZ promoter ($P_{lacZ}$)-apramycin resistant gene-DhaK gene amino terminus (dhaK') was constructed.

The plasmid was treated with BamHI-BglII, and the collected DNA fragment was introduced into the *Klebsiella pneumoniae* Cu strain by electroporation. Then, recombinant strains that formed colonies in a medium supplemented with apramycin were isolated from the Cu strain cells. As a result, a recombinant *Klebsiella pneumoniae* AK strain (KCTC 11419BP) with deletions of the DhaB enzyme reactivation gene, DhaT gene, DhaR regulator and DhaD gene of the dha regulon and insertions of the lacZ promoter and the apramycin resistant gene was obtained.

(3) Overexpression of Gene Encoding Propanediol Utilization Protein in Mutant Strain in which Anaerobic Metabolic Pathway of Glycerol was Blocked Each of the plasmid pVOTLp containing the gene encoding propanediol utilization protein and the plasma DNA containing the DhaB reactivation enzyme gene and the 1,3-propanediol oxidoreductase gene was introduced by electroporation into each of the *Klebsiella pneumoniae* Cu and AK strains. The recombinant strain AK-VOTLp constructed in this Example was deposited at the Biological Resource Center in the Korea Research Institute of Bioscience and Biotechnology under accession number KCTC 11689BP.

TABLE 1

Recombinant strains and plasmid DNAs used or constructed in the present invention

| Strains | |
| --- | --- |
| *E. coli* DH5a | Cloning Host |
| *K. pneumoniae* | TetR contained Plasmid DNA curing |
| Cu | *K. pneumoniae* MGH 78578 |
| *K. pneumoniae* AK | (orfY-dhaT-orfW-orfX-dhaR-dhaD)::PLacZ-AprR |
| Plasmids | |
| pV | pBR322 |
| pVO | pBR322-PLacZorfW-orfX |
| pVOT | pBR322-PLacZorfW-orfX-PLacZdhaT |
| pVOTLp | pBR322-PLacZorfW-orfX-PLacZpduP-PLacZdhaT |

Example 2

Culture of *Klebsiella pneumoniae* Recombinant Strain in which Gene Encoding Propanediol Utilization Protein was Overexpressed The recombinant strain prepared in Example 1 was cultured in 50 ml of a medium containing glycerol as a single carbon source at 37° C. for 20 hours at 120 rpm, and then the production of 3-hydroxypropionic acid was analyzed by chromatography.

The medium used in the culture process had the following composition:

A 0.1M potassium phosphate buffer (pH 7.0) supplemented with 20 g/L glycerol or glucose and then supplemented with 2 g/l $(NH_4)_2SO_4$, 0.2 g/l $MgSO_4$, 0.002 g/l $CaCl_2 2H_2O$, 1 g/l yeast extract, 1 ml iron solution [5 g/l $FeSO_4 7H_2O$, 4 ml HCl (37%, w/v)] and 1 ml trace element solution [70 mg/l $ZnCl_2$, 100 mg/l $MnCl_2 4H_2O$, 60 mg/l $H_3BO_3$, 200 mg/l $CoCl_2 4H_2O$, 20 mg/l $CuCl_2 2H_2O$, 25 mg/l $NiCl_2 6H_2O$, 35 mg/l $Na_2MoO_4 2H_2O$, 4 ml HCl (37%, w/v)]. In addition, 0.5 mM of IPTG and 10 μg/ml of antibiotic tetracycline were added to the medium.

The chromatography was performed using an Aminex HPX-87H column (Bio-Rad, 300 mm×78 mm) with an Agilent 1200 series refractive index detector (RID). As the mobile phase, 0.5 mM $H_2SO_4$ (flow rate: 0.8 ml/min) was used, and as a standard, commercially available 3-hydroxypropionic acid (Tokyo Chemical Industry Co., LTD) was used.

As a result, it was shown that the production of 3-hydroxypropionic acid in the recombinant strain in which the gene encoding propanediol utilization protein had been overexpressed increased twice or more (Table 2).

In addition, it was shown that the production of 3-hydroxypropionic acid in the Cu/pVOTLp strain obtained by introducing the pduP gene into the parent strain (Cu) in which the glycerol oxidative pathway was not blocked was higher than that in the strain containing no pduP gene (Table 3).

TABLE 2

Contents of metabolic products produced by flask culture of *Klebsiella pneumoniae* AK-derived recombinant strain

| Metabolic products (g/L) | AK/pVOT | AK/pVOTLp |
|---|---|---|
| Remaining glycerol | 5.4 | 8.3 |
| 1,3-propanediol | 7.3 | 5.6 |
| 3-hydroxypropionic acid | 0.4 | 0.9 |
| 2,3-butanediol | 0 | 0 |
| Ethanol | 0 | 0 |
| Lactic acid | 0.2 | 0.2 |
| Succinic acid | 0.2 | 0.1 |
| Acetic acid | 1.7 | 1.6 |

TABLE 3

Contents of metabolic products produced by flask culture of *Klebsiella pneumoniae* Cu-derived recombinant strain

| Metabolic products (g/L) | Cu/pVOT | Cu/pVOTLp |
|---|---|---|
| Remaining glycerol | 0 | 0 |
| 1,3-propanediol | 8.7 | 8.2 |
| 3-hydroxypropionic acid | 0.2 | 0.7 |
| Lactic acid | 0.2 | 0 |
| Acetic acid | 2.0 | 0 |

Example 3

Culture of *Klebsiella pneumoniae* AK-VOTLp in 5-L Fermenter

The *Klebsiella pneumoniae* AK-VOTLp strain was cultured in a 5-L fermenter, and the degree of growth of the strain was examined. In addition, the amount of glycerol remaining in the culture supernatant and the production of metabolic products, including 3-hydroxypropionic acid and 1,3-propanediol, were analyzed by chromatography.

The medium used in the culture process had the following composition:

20 g/l glycerol, 3.4 g/l $K_2HPO_4$, 1.3 g/l $KH_2PO_4$, 0.2 g/l $MgSO_4$, 0.002 g/l $CaCl_2 2H_2O$, 1 g/l yeast extract, 1 ml iron solution [5 g/l $FeSO_4 7H_2O$, 4 ml HCl (37%, w/v)] and 1 ml tract element solution [70 mg/l $ZnCl_2$, 100 mg/l $MnCl_2 4H_2O$, 60 mg/l $H_3BO_3$, 200 mg/l $CoCl_2 4H_2O$, 20 mg/l $CuCl_2 2H_2O$, 25 mg/l $NiCl_2 6H_2O$, 35 mg/l $Na_2MoO_4 2H_2O$, 4 ml HCl (37%, w/v)].

TABLE 4

Contents of metabolic products produced by culture of *Klebsiella pneumoniae* AK-VOTLp recombinant strain in 5-L fermenter

| Metabolic products (g/L) | 0 h | 3 h | 6 h | 10 h | 15 h | 20 h | 24 h | 28 h | 36 h |
|---|---|---|---|---|---|---|---|---|---|
| Remaining glycerol | 20.3 | 20.2 | 15.8 | 10.0 | 7.9 | 3.3 | 0.2 | 0 | 0 |
| 1,3-propanediol | 0 | 0 | 0.6 | 2.6 | 6.1 | 7.8 | 7.8 | 8.6 | 6.2 |
| 3-hydroxypropionic acid | 0 | 0 | 0 | 0 | 0.4 | 0.6 | 1.1 | 2.2 | 2.2 |
| 2,3-butanediol | 0 | 0 | 0 | 0 | 0 | 0 | 0 | 0 | 0 |
| Ethanol | 0 | 0 | 0 | 0 | 0 | 0 | 0 | 0 | 0 |
| Lactic acid | 0 | 0 | 0 | 0.2 | 0.2 | 0.2 | 0.2 | 0.2 | 0.2 |
| Succinic acid | 0 | 0 | 0 | 0 | 0 | 0 | 0 | 0 | 0 |
| Acetic acid | 0 | 0 | 0 | 1.1 | 2.0 | 2.3 | 2.3 | 2.9 | 2.4 |
| 3-HP/glycerol (mol/mol) | 0 | 0 | 0 | 0 | 0.03 | 0.04 | 0.06 | 0.11 | 0.11 |
| 3-HP productivity (g/Lh) | 0 | 0 | 0 | 0 | 0.03 | 0.03 | 0.05 | 0.08 | 0.06 |

The culture process was carried out under the following conditions: the effective volume of the 5 L fermenter: 2 L; the final concentration of IPTG: 0.5 mM; the final concentration of tetracycline: 10 μg/L; inoculation concentration: 1%; culture temperature: 37° C.; stirring rate: 200 rpm; and aeration rate: 0.5 vvm.

As a result, as shown in FIG. 3, the strain completely consumed glycerol at 28 hours of culture, in which the production, conversion rate and productivity of 3-hydroxypropionic acid were 2.2 g/L, 0.11 (mol/mol) and 0.08 g/Lh, respectively.

[Deposit of Microorganisms]

Depository Institution: Korea Research Institute of Bioscience and Biotechnology;

Accession Number: KCTC 11689BP;

Deposit Date Apr. 26, 2010.

INDUSTRIAL APPLICABILITY

As described above, according to the present invention, 3-hydroxypropionic acid can be produced in high yield from glycerol without having to add expensive coenzyme B12.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

The invention claimed is:

1. A *Klebsiella pneumoniae* mutant obtained by deleting a glycerol dehydrogenase gene (DhaD), a transcriptional activator gene (DhaR), a 1,3-propanediol oxidoreductase gene (DhaT) and a glycerol dehydratase reactivation factor II gene (DhaBA2) from *Klebsiella pneumoniae* and introducing a 1,3-propanediol oxidoreductase-encoding gene, an aldehyde dehydrogenase-encoding gene and a gene encoding propanediol utilization protein (PduP) into the *Klebsiella pneumoniae* wherein the *Klebsiella pneumoniae* is *Klebsiella pneumoniae* AK-VOTLp (KCTC 11689 BP).

2. A method for preparing a *Klebsiella pneumoniae* mutant, the method comprising deleting a glycerol dehydrogenase gene (DhaD), a transcriptional activator gene (DhaR), a 1,3-propanediol oxidoreductase gene (DhaT) and a glycerol dehydratase reactivation factor II gene (DhaBA2) from *Klebsiella pneumoniae* and introducing a 1,3-propanediol oxidoreductase -encoding gene, an aldehyde dehydrogenase-encoding gene and a gene encoding propanediol utilization protein (PduP) into the *Klebsiella pneumoniae*, wherein the *Klebsiella pneumoniae* is *Klebsiella pneumoniae* AK-VOTLp (KCTC 11689 BP).

3. A method for producing 3-hydroxypropionic acid, comprising the steps of:
(a) culturing the *Klebsiella pneumoniae* mutant of claim 1 in a glycerol-containing medium, thereby producing 3-hydroxypropionic acid; and
(b) recovering the produced 3-hydroxypropionic acid.

* * * * *

SEQUENCE LISTING

```
<160> NUMBER OF SEQ ID NOS: 10

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
tctagaatgc agattaatga tattgaaagt gct                                    33

<210> SEQ ID NO 2
<211> LENGTH: 39
<212> TYPE: DNA
<213> ORGANISM: Artificial
<220> FEATURE:
<223> OTHER INFORMATION: primer

<400> SEQUENCE: 2
ggatccctcg agttaatacc agttacgtac tgagaatcc                              39

<210> SEQ ID NO 3
<211> LENGTH: 27
<212> TYPE: DNA
<213> ORGANISM: Artificial
<220> FEATURE:
<223> OTHER INFORMATION: primer

<400> SEQUENCE: 3
tctagaatga aaagatcaaa acgattt                                           27

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
ggatccgtca gcggcaatct gcac                                              24

<210> SEQ ID NO 5
<211> LENGTH: 26
<212> TYPE: DNA
<213> ORGANISM: Artificial
<220> FEATURE:
<223> OTHER INFORMATION: primer

<400> SEQUENCE: 5
```

```
aagcttcatg ctctccggcg cctgtc                                          26

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
agatctattt ggtccagcga gctgaagc                                        28

<210> SEQ ID NO 7
<211> LENGTH: 26
<212> TYPE: DNA
<213> ORGANISM: Artificial
<220> FEATURE:
<223> OTHER INFORMATION: primer

<400> SEQUENCE: 7
agatctcctg ggatttcgcg acggca                                          26

<210> SEQ ID NO 8
<211> LENGTH: 27
<212> TYPE: DNA
<213> ORGANISM: Artificial
<220> FEATURE:
<223> OTHER INFORMATION: primer

<400> SEQUENCE: 8
aagctttcga caatcggttt taaggtg                                         27

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9
gttaacctga cgccgttgga tacacc                                          26

<210> SEQ ID NO 10
<211> LENGTH: 32
<212> TYPE: DNA
<213> ORGANISM: Artificial
<220> FEATURE:
<223> OTHER INFORMATION: primer

<400> SEQUENCE: 10
agatctaaaa gcttatgagc tcagccaatc ga                                   32
```